United States Patent
Suzuki et al.

(10) Patent No.: US 12,402,965 B2
(45) Date of Patent: Sep. 2, 2025

(54) MEDICAL OPERATION APPARATUS

(71) Applicant: RIVERFIELD INC., Tokyo (JP)

(72) Inventors: Masataka Suzuki, Tokyo (JP); Kotaro Tadano, Tokyo (JP)

(73) Assignee: RIVERFIELD INC., Tokyo (JP)

( * ) Notice: Subject to any disclaimer, the term of this patent is extended or adjusted under 35 U.S.C. 154(b) by 434 days.

(21) Appl. No.: 18/094,141

(22) Filed: Jan. 6, 2023

(65) Prior Publication Data

US 2023/0149107 A1 May 18, 2023

Related U.S. Application Data

(63) Continuation of application No. PCT/JP2020/026766, filed on Jul. 8, 2020.

(51) Int. Cl.
*A61B 34/00* (2016.01)
*A61B 34/37* (2016.01)
*A61B 34/20* (2016.01)

(52) U.S. Cl.
CPC .............. *A61B 34/37* (2016.02); *A61B 34/74* (2016.02); *A61B 34/75* (2016.02); *A61B 34/76* (2016.02); *A61B 2034/2059* (2016.02)

(58) Field of Classification Search
CPC ......... A61B 34/37; A61B 34/74; A61B 34/75; A61B 34/76; A61B 2034/2059; A61B 2017/00424; A61B 34/70

(Continued)

(56) References Cited

U.S. PATENT DOCUMENTS 6,039,752 A * 3/2000 Kimura .............. A61B 17/2909
606/205
8,521,331 B2 * 8/2013 Itkowitz ................. A61B 34/30
606/1

(Continued)

FOREIGN PATENT DOCUMENTS

JP 2013-510671 A 3/2013
JP 2019-500914 A 1/2019

(Continued)

OTHER PUBLICATIONS

Notice of Reasons for Refusal of Japanese Application No. 2020-562223 dated Dec. 14, 2021.

(Continued)

*Primary Examiner* — Jaime Figueroa
(74) *Attorney, Agent, or Firm* — Sughrue Mion, PLLC

(57) ABSTRACT

A medical operation apparatus includes a body graspable by an operator, an operation part that is arranged to enable a part of the operation part to be moved relative to the body, and a holder that receives the fingers of the operator and transmits a movement of the fingers to the operation part. The holder includes a contact portion that comes in contact with the body, and a connector that supports a relative posture of the holder and the operation part so as to change the relative posture in accordance with a posture change of the fingers of the operator. In a relative arrangement position of the operation part and the body, when the relative posture of the holder and the operation part is changed, an amount of change in the relative arrangement position of the body and the operation part is within a specified permissible range.

20 Claims, 10 Drawing Sheets

(58) Field of Classification Search
USPC .............. 700/245–264; 318/568.11–568.25; 74/490.01, 479.01
See application file for complete search history.

(56) References Cited

U.S. PATENT DOCUMENTS

| | | | | |
|---|---|---|---|---|
| 8,831,782 | B2* | 9/2014 | Itkowitz | A61B 34/30 606/1 |
| 10,058,347 | B2* | 8/2018 | Hirai | A61B 90/50 |
| 10,966,798 | B2* | 4/2021 | Tesar | H04N 13/344 |
| 11,712,314 | B2* | 8/2023 | Thompson | B25J 13/02 606/1 |
| 2009/0030428 | A1* | 1/2009 | Omori | A61B 34/70 606/130 |
| 2011/0118748 | A1 | 5/2011 | Itkowitz | |
| 2012/0041595 | A1* | 2/2012 | Greeley | B25J 3/04 700/264 |
| 2014/0018960 | A1* | 1/2014 | Itkowitz | A61B 90/98 700/264 |
| 2014/0048174 | A1* | 2/2014 | Lanigan | A61M 5/16809 141/349 |
| 2014/0165770 | A1* | 6/2014 | Abri | B25J 13/025 606/130 |
| 2015/0335347 | A1 | 11/2015 | Hira et al. | |
| 2017/0143442 | A1* | 5/2017 | Tesar | H04N 23/63 |
| 2018/0147019 | A1* | 5/2018 | Farritor | B25J 9/161 |
| 2018/0296286 | A1 | 10/2018 | Peine et al. | |
| 2020/0390510 | A1* | 12/2020 | Thompson | A61B 34/35 |

FOREIGN PATENT DOCUMENTS

| | | |
|---|---|---|
| WO | 2014/196419 A1 | 12/2014 |
| WO | 2018/102430 A1 | 6/2018 |
| WO | 2019/093020 A1 | 5/2019 |

OTHER PUBLICATIONS

International Search Report of PCT/JP2020/026766 dated Oct. 6, 2020 [PCT/ISA/210].
International Preliminary Report on Patentability issued Jan. 10, 2023 in International Application No. PCT/JP2020/026766.
Written Opinion of the International Searching Authority dated Oct. 6, 2020 in International Application No. PCT/JP2020/026766.

* cited by examiner

MEDICAL OPERATION APPARATUS

CROSS REFERENCE TO RELATED APPLICATION

This application is a continuation application of International Patent Application No. PCT/JP2020/026766 filed on Jul. 8, 2020, in the Japan Patent Office, the contents of which being incorporated by reference herein in its entirety.

BACKGROUND

1. Field

The present disclosure relates to a medical operation apparatus that allows to reflect a grasping operation performed by an operator.

2. Description of Related Art

In recent years, endoscopic surgery using a master-slave type surgical assist robot has become widely available. Here, the master means a medical operation apparatus that remotely controls a slave, and the slave means a surgical device that performs surgery in accordance with instructions from the master.

The above-described surgical assist robot has a configuration in which in response to an operator moving a grip of the master, slave forceps are moved in conjunction with the grip. However, it is difficult operators with different finger sizes and finger lengths to properly reflect a content of the movement resulting in unintentional operation.

SUMMARY

It is an aspect to provide a medical operation apparatus which may easily inhibit an unintentional operation from being reflected in the medical operation apparatus.

According to an aspect of one or more embodiments, there is provided a medical operation apparatus comprising a body to be grasped by an operator; an operation part arranged to enable at least a part of the operation part to be moved, by the operator, closer to and away from the body; and a holder configured to hold fingers of the operator grasping the body, the holder being configured to transmit a movement of the fingers to the operation part. The holder comprises a contact portion configured to be in contact with the body when the operation part is moved closer to the body, and a connector supporting a relative posture of the holder and the operation part so as to change the relative posture in accordance with a posture change of the fingers of the operator, wherein, in a relative arrangement position of the operation part and the body with which the contact portion is in contact, when the relative posture of the holder and the operation part is changed, an amount of change in the relative arrangement position of the body and the operation part is within a specified permissible range.

According to another aspect of one or more embodiments, there is provided a medical operation apparatus comprising a body; an operation part connected to the body such that at least a portion of the operation part is movable with respect to the body; and a finger holder configured to receive fingers of an operator who grasps the body, the finger holder configured to transmit a movement of the fingers to the operation part and comprising a contact portion configured to contact with the body when the operation part is moved toward the body, and a connector rotatably supporting the contact portion, wherein, when the operation part contacts the body and a relative posture of the finger holder and the operation part is changed, an amount of change in a relative position of the body relative to the operation part is within a threshold range.

According to yet another aspect of one or more embodiments, there is provided a medical operation apparatus comprising a body including a shaft and a cylindrical grip attached to one end of the shaft; an operating part movable relative to the body; a finger holder that is slidable along the operating part, the finger holder comprising a connector, and a contact portion that is rotatably connected to the connector and that contacts the shaft of the body when the operating part is moved relative to the body, wherein, when the contact portion contacts the shaft, the contact portion is rotatable such that a distance between a central axis of the connector and a contact point between the contact portion and the shaft remains constant.

BRIEF DESCRIPTION OF THE DRAWINGS

The above and/or other aspects will become apparent and more readily appreciated from the following description of various embodiments, taken in conjunction with the accompanying drawings, in which.

DETAILED DESCRIPTION

Figure 1:
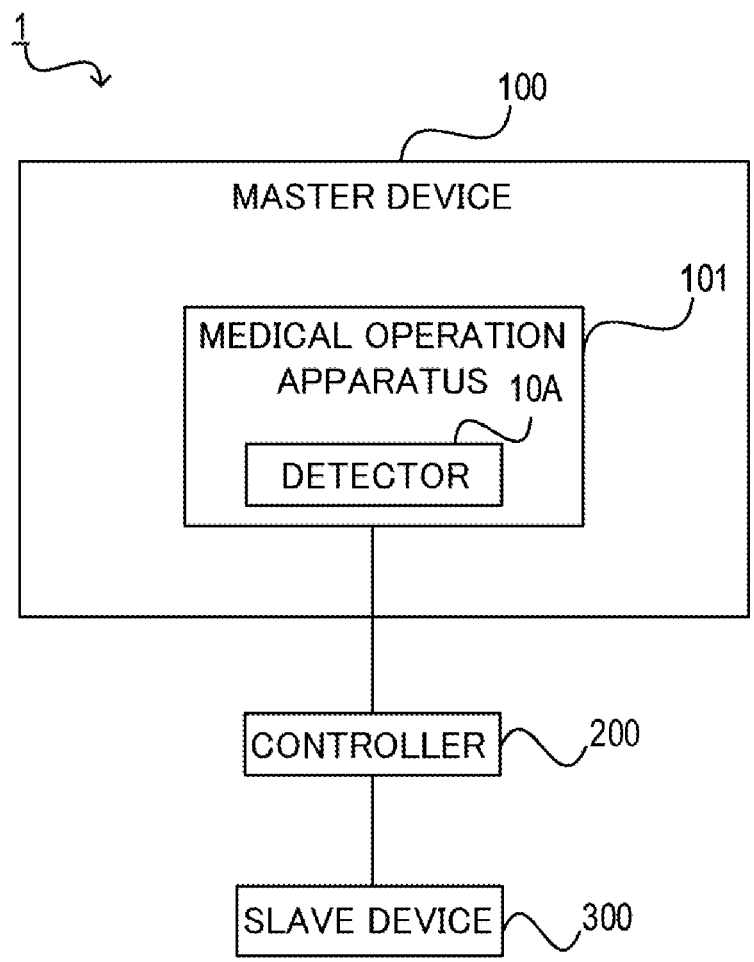
FIG. 1 is a block diagram showing one example of an overall configuration of a surgical assist robot, according to some embodiments.

As described above, a surgical assist robot may have a configuration in which in response to an operator moving a grip of the master, slave forceps are moved in conjunction with the grip. Therefore, the operator who operates the master-slave type surgical assist robot can operate the forceps of the surgical assist robot at will as if the forceps are part of him/herself. Specifically, a medical operation apparatus may allow an operator to hold a body so as to wrap the body with his/her palm, place his/her fingers onto an engagement portion of an operation part, and move his/her fingers in this state, thereby reflecting the content of the movement.

However, in the above-described medical operation apparatus, a distance between the body and the engagement portion is fixed. Thus, it is difficult for operators with different finger sizes and finger lengths to properly reflect the content of the movement.

It is conceivable to provide an adjustment mechanism to adjust the distance between the body and the engagement portion arranged in the operation part. However, if the adjustment mechanism is moved by an unintentional operation by the operator and the operation part is moved in conjunction with the movement of the adjustment mechanism, the content of the movement is reflected based on the unintentional movement of the operation part. As a result, the slave may be remote-controlled based on the unintentional operation by the operator.

In one aspect of the present disclosure, it is advantageous to easily inhibit the unintentional operation from being reflected in the medical operation apparatus that is the master.

According to some embodiments, a medical operation apparatus may be configured to acquire an operation performed by an operator, the medical operation apparatus comprising a body, an operation part, and a holder. The operator grasps the body. The operation part is arranged so as to enable at least a part of the operation part to be moved closer to and away from the body by the operator. The holder is configured to hold fingers of the operator grasping the body, and the holder is configured to transmit a movement of the fingers to the operation part. The holder comprises a contact portion and a connector. The contact portion is configured to be in contact with the body when the operation part is moved closer to the body. The connector supports a relative posture of the holder and the operation part so as to change the relative posture in accordance with a posture change of the fingers of the operator. In the relative arrangement position of the body with which the contact portion is in contact and the operation part, when the relative posture of the holder and the operation part is changed, an amount of change in the relative arrangement position of the body and the operation part is within a specified permissible range.

According to this configuration, the connector supports the relative posture of the holder and the operation part so as to change the relative posture in accordance with the posture change of the fingers of the operator. Therefore, the device is configured to be available for multiple operators with different finger sizes.

Furthermore, in a state where the contact portion is in contact with the body, even if the operator performs an unintentional operation due to a force applied to the fingers and the posture of the operator's fingers and the relative posture of the holder and the operation part are changed, the amount of change in the relative arrangement position of the body and an operation part is within the specified permissible range.

This configuration makes it possible to inhibit the operation part from moving equal to or more than the permissible range even if the unintentional operation is performed by the operator, and makes it easy to inhibit the operation part from moving equal to or more than the permissible range. As a result, in the medical operation apparatus that is the master, it is easier to inhibit the unintentional operation by the operator from being reflected.

According to some embodiments, a sensor may be configured to detect the relative arrangement position of the operation part to the body. The permissible range may be less than a minimum value of an amount of change, detectable by the sensor, between the body and the operation part.

In this configuration, the permissible range is set to less than the minimum value of the amount of change detectable by the sensor. Thus, it is possible to inhibit the operation part from moving equal to or more than the minimum amount of change detectable by the sensor even if the operator performs the unintentional operation. This configuration makes it easy to inhibit the detector from detecting the unintentional operation by the operator as a grasping operation.

According to some embodiments, the contact portion may comprise a convex surface formed into a convex shape, and the amount of change in the relative arrangement position of the body and the operation part, based on a variation in a distance between the convex surface and a center of a posture change of the holder in the connector, may be within the specified permissible range.

In this configuration, the amount of change in the relative arrangement position of the body and the operation part, based on the variation in the distance between the convex surface of the contact portion and the center of the posture change of the holder in the connector, is within the specified permissible range. This configuration makes it is easy to inhibit the unintentional operation by the operator from being reflected as the grasping operation.

According to some embodiments, the contact portion may comprise contact flat surfaces, and the amount of change in the relative arrangement position of the body and the operation part, based on a variation in a distance between each of the contact flat surfaces and a center of a posture change of the holder in the connector, may be within the specified permissible range.

In this configuration, the amount of change in the relative arrangement position of the body and the operation part, based on the variation in the distance between each of the flat surfaces of the contact portion and the center of the posture change of the holder in the connector, is within the specified permissible range. This configuration makes it is easy to inhibit the unintentional operation by the operator from being reflected as the grasping operation.

According to some embodiments, the body comprises a concave surface formed into a concave shape in an area to be in contact with the contact portion, and when the contact portion is in contact with the concave surface, the amount of change in the relative arrangement position of the body and the operation part, based on a variation in a distance between the concave surface and a center of a posture change of the holder in the connector, may be within the specified permissible range.

In this configuration, when the contact portion is in contact with the concave surface formed into a curved surface in the body, the amount of change in the relative arrangement position of the body and the operation part, based on the variation in the distance between the concave surface and the center of the posture change of the holder in the connector, is within the specified permissible range. This configuration makes it is easy to inhibit the unintentional operation by the operator from being reflected as the grasping operation.

According to some embodiments, the body may comprise body flat surfaces forming a concave shape in the area to be in contact with the contact portion, and when the contact portion is in contact with any of the body flat surfaces, the amount of change in the relative arrangement position of the body and the operation part, based on a variation in a distance between each of the body flat surfaces and a center of a posture change of the holder in the connector, may be within the specified permissible range.

In this configuration, when the contact portion is in contact with the concave surface formed by the flat surfaces in the body, the amount of change in the relative arrangement position of the body and the operation part, based on the variation in the distance between each of the body flat surfaces and the center of the posture change of the holder in the connector, is within the specified permissible range. This configuration makes it is easy to inhibit the unintentional operation by the operator from being reflected as the grasping operation.

According to some embodiments, the operation part may be formed into a long shape, and the connector connects the holder and the operation part so that an arrangement position of the holder along a longitudinal direction of the operation part having a long shape is changeable.

In this configuration, the connector connects the holder and the operation part so that an arrangement position of the holder along the longitudinal direction of the operation part having a long shape is changeable. Therefore, the arrangement position of the holder can be varied relative to the operation part in accordance with the size or the like of the operator's fingers.

1. Configuration

The surgical assist robot 1 may be a master-slave robot for endoscopic surgery and the like. The surgical assist robot 1 includes a master device and a slave device. The operation that has been reflected in the master device is transmitted to the slave device by communications, and the slave device works.

The surgical assist robot 1 will be described with reference to FIG. 1.

The surgical assist robot 1 comprises a master device 100, a controller 200, and a slave device 300.

A medical operation apparatus 101 is a part of the master device 100, and is configured to detect a grasping operation performed by an operator, including a medical worker. The medical operation apparatus 101 is configured to be able to reflect at least the grasping operation performed by the operator. The detector 10A is configured to detect the operation performed by the operator with a sensor arranged in a body, for example.

The controller 200 is configured to control the slave device 300 based on the operation performed by the operator that has been detected by the medical operation apparatus 101. The controller 200 comprises various control structures and control methods in accordance with the configuration of the slave device 300.

The slave device 300 is a slave-side device in the surgical assist robot 1, and is configured to perform a grasping action based on the control by the controller 200. For example, the slave device 300 may be a pair of forceps. Examples of a target grasped by the slave device 300 may include blood vessels and/or organs of a patient's body.

The target grasped by the slave device 300 is not limited to the blood vessels or the organs of the patient's body, and may include various targets that can be grasped by the slave device 300.

Here, in addition to the grasping operation performed by the operator, the medical operation apparatus 101 may detect operations to move the slave device 300 and to change the posture of the slave device 300. Thus, the controller 200 may control the movement and the posture change of the slave device 300 in addition to the grasping action. The medical operation apparatus 101 is configured to be operated by the operator's right hand; however, the medical operation apparatus 101 may be configured to be operated by the left hand.

Figure 2:
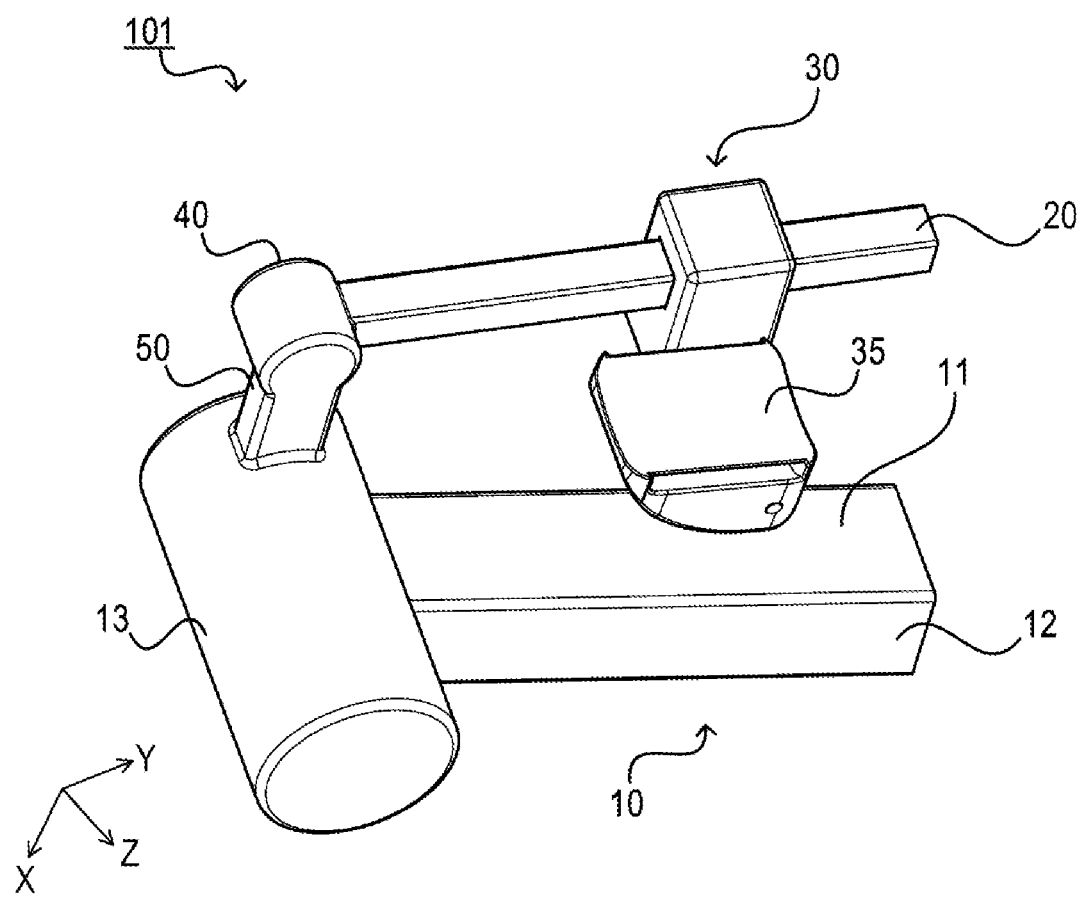
FIG. 2 is a perspective view showing an overview of a medical operation apparatus, according to some embodiments.
Figure 3:
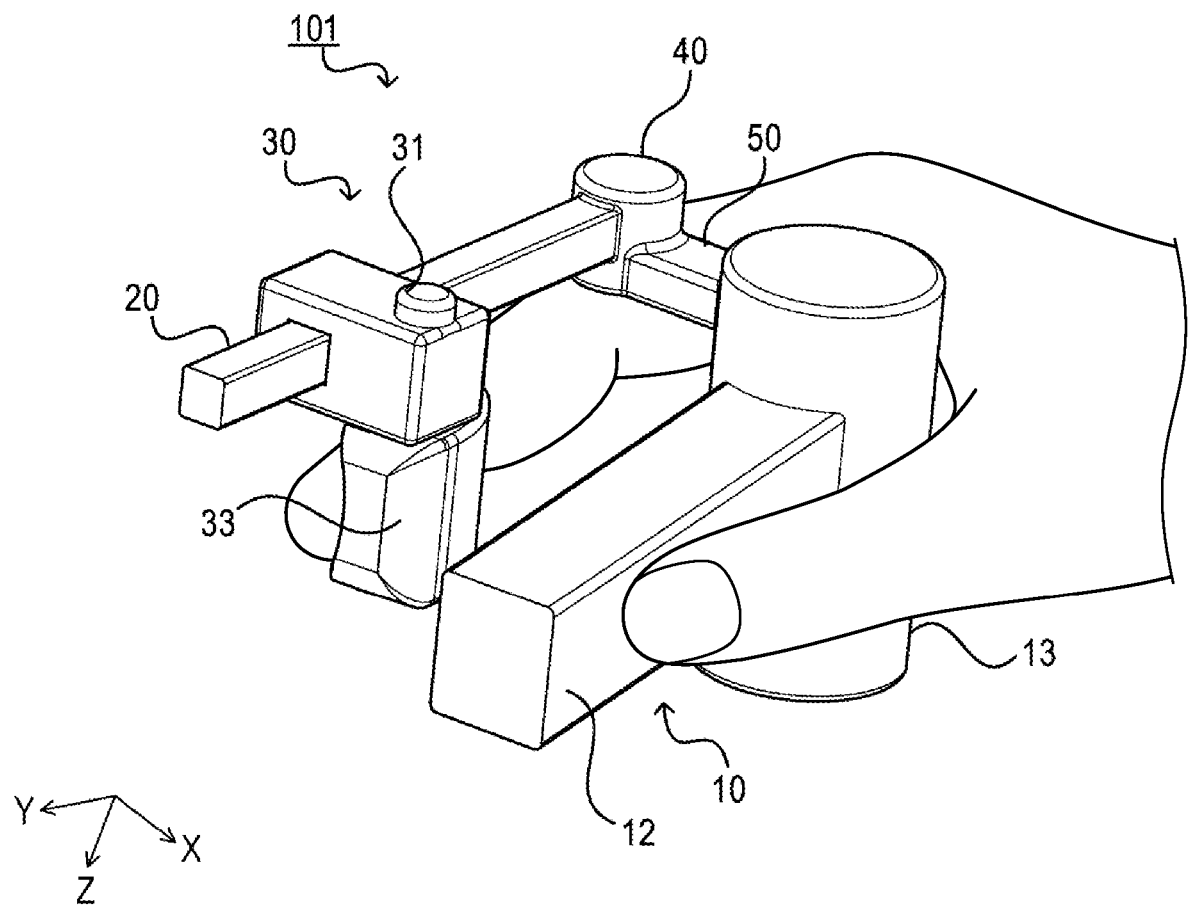
FIG. 3 is another perspective view showing an overview of the medical operation apparatus, according to some embodiments.
Figure 4:
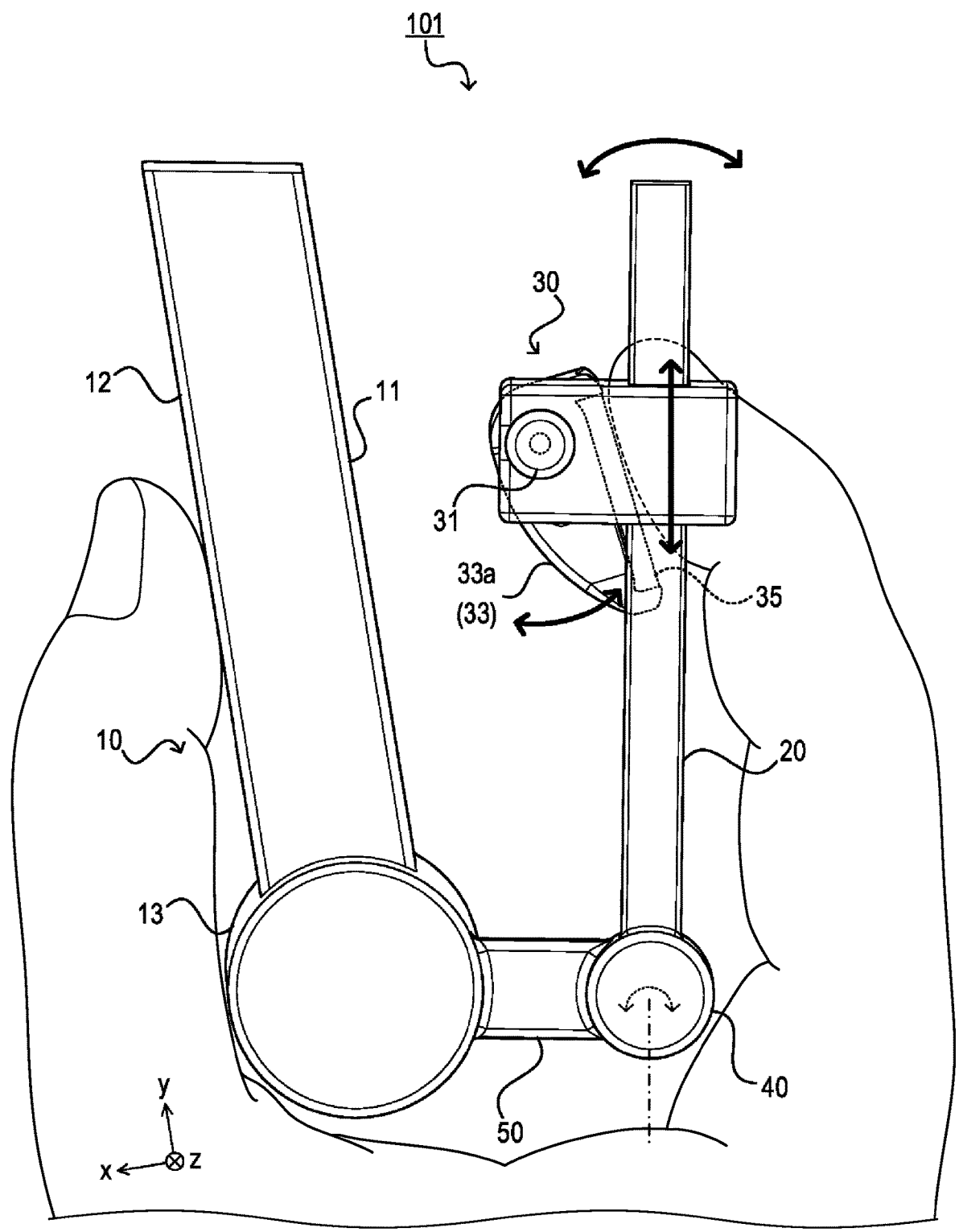
FIG. 4 is a plan view showing an overview of the medical operation apparatus, according to some embodiments.
Figure 5:
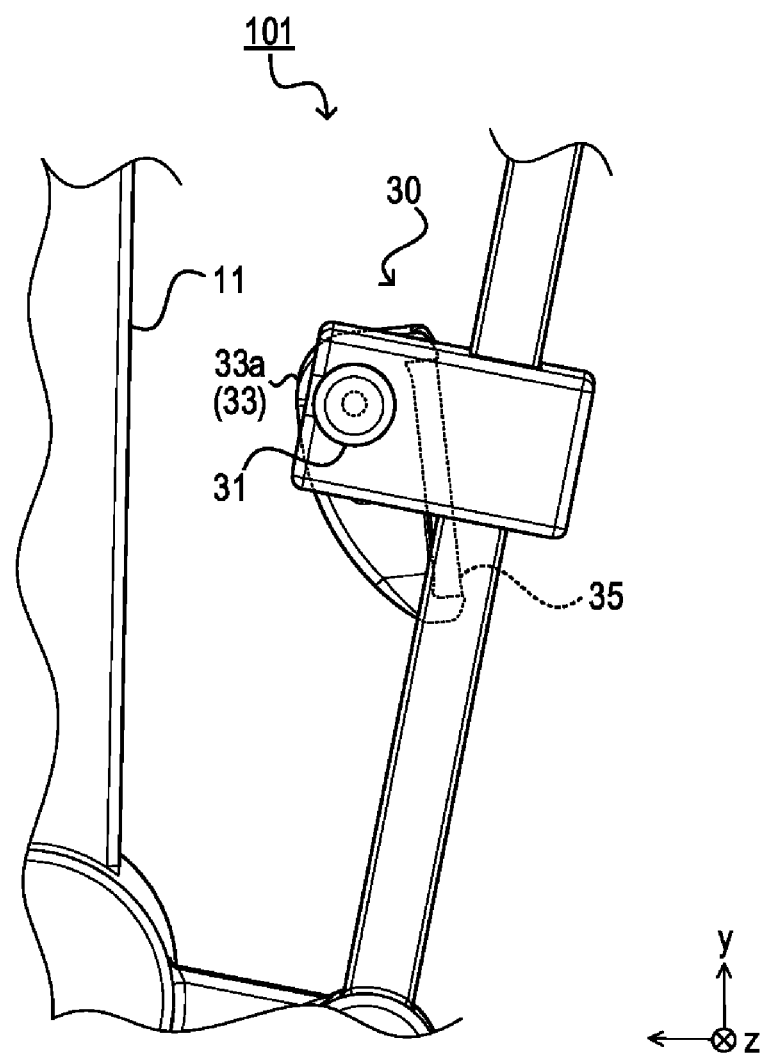
FIG. 5 shows an example of a holder, according to some embodiments.

FIG. 2 is a perspective view showing an overview of a medical operation apparatus, according to some embodiments. FIG. 3 is another perspective view showing an overview of the medical operation apparatus, according to some embodiments. FIG. 4 is a plan view showing an overview of the medical operation apparatus, according to some embodiments. FIG. 5 shows an example of a holder, according to some embodiments.

As shown in FIG. 1 to FIG. 5, the medical operation apparatus 101 according to some embodiments comprises a body 10, an operation part 20, a holder 30, a rotating portion 40, a detector 10A, and a supporting portion 50. The illustration of the structure in which the medical operation apparatus 101 is connected to the master device 100 is omitted in FIGS. 1-5.

The body 10 is a part to be grasped by the operator. The body 10 comprises a long portion 12 formed into a long shape such as a columnar shape, and a grip 13 protruding from an end of the long portion 12. In some embodiments, the long portion 12 may be a bar, a shaft, or a beam. In the body 10, the grip 13 is formed at one end of the long shape. The body 10 is configured to be held by the operator with the grip 13 being grasped.

Hereinafter, a longitudinal direction of the long portion 12 is assumed as a y-axis direction. The direction from the end with the grip 13 to the other end in the long portion 12 is assumed as a positive direction of the y-axis. An extending direction of the grip 13 perpendicular to the y-axis direction is assumed as a z-axis direction. The direction away from the long portion 12 is assumed as a positive direction of the z-axis direction. A direction perpendicular to each of the y-axis direction and the z-axis direction is assumed as an x-axis direction. The x-axis, the y-axis, and the z-axis are configured in accordance with a right-handed coordinate system.

The grip 13 is formed into a substantially columnar shape. In some embodiments, the grip 13 may be, for example, a cylindrical shaft.

The peripheral surface of the grip 13 may be formed into a shape easily held by the operator's right hand. Specifically, the peripheral surface of the grip 13 may have a concave shape suitable for the shape of the right hand.

The grip 13 comprises a supporting portion 50 that is arranged near the long portion 12 and that has a long shape extending toward a substantially x-axis negative direction. The supporting portion 50 comprises a first end that is on a grip 13 side and that is connected to the grip 13. The supporting portion 50 comprises a second end that is opposite the first end and that comprises a rotating portion 40.

The operation part 20 is used to reflect the grasping operation performed by the operator. The operation part 20 has a long shape extending from the rotating portion 40. In some embodiments, the operation part may be, for example, a beam, a rod, or a shaft.

The rotating portion 40 is arranged between the supporting portion 50 and the operation part 20 and comprises a rotation axis extending in the substantially z-axis direction. The rotating portion 40 allows the supporting portion 50 and the operation part 20 to relatively move around the rotation axis. The rotating portion 40 rotates around the rotation axis, thereby enabling a change in the angle formed by a longitudinal direction of the supporting portion 50 and a longitudinal direction of the operation part 20.

In other words, when the operation part 20 rotates around the rotation axis of the rotating portion 40, the operation part 20 moves around the rotation axis. Due to the rotation, the operation part 20 moves closer to or away from the body 10.

The detector 10A is configured to detect the angle formed by the longitudinal direction of the supporting portion 50 and the longitudinal direction of the operation part 20. The detector 10A is configured to output, to the controller 200, the detected angle as a detection signal. The detector 10A may be arranged any position as long as the detector 10A can detect the angle formed by the longitudinal direction of the supporting portion 50 and the longitudinal direction of the operation part 20. The detector 10A is an angle sensor for measuring the angle formed by the longitudinal direction of the supporting portion 50 and the longitudinal direction of the operation part 20. The detector 10A may be a rotary encoder or other angle sensors.

The holder 30 is configured to hold fingers of the operator grasping the body 10. The holder 30 is configured to transmit, to the operation part 20, the movement of the fingers. The holder 30 is provided to the operation part 20, and is configured such that the arrangement position thereof can be changed along the longitudinal direction of the operation part 20. In other words, the holder 30 may slide along the operation part 20. In operation, a hand of the operator may grasp the body 10 such that the operator's palm would contact the grip 13, the operator's thumb would rest on the body 10 and the operator's fingers would wrap around and contact the holder 30.

The holder 30 comprises a connector 31, a contact portion 33, and a transmitting portion 35.

The connector 31 is connected to the operation part 20. The connector 31 may be connected to the operation part 20 so that the holder 30 is movable along the longitudinal direction of the operation part 20. In other words, the operation part 20 may slide along the beam, rod, or shaft.

The connector 31 has a rotation axis along the substantially z-axis direction. The rotation axis allows the contact portion 33 and the transmitting portion 35 to rotate relative to the connector 31.

The connector 31 supports a relative posture between the contact portion 33/the transmitting portion 35 and the operation part 20 so as to change the relative posture in accordance with the posture change of the fingers on the operation part 20.

When the operation part 20 comes closer to the long portion 12 of the body 10, the contact portion 33 is in contact with a body right surface 11 of the long portion 12. The body right surface 11 of the body 10 as used herein is the right surface of the body 10, i.e. a side surface located on an x-axis negative side.

Specifically, the contact portion 33 is arranged so as to be positioned on an x-axis positive side relative to the connector 31. When positioned on the x-axis positive side, the contact portion 33 comprises a convex surface 33a formed into a convex shape that is swelled in an x-axis positive direction. That is, the contact portion 33 comprises the convex surface 33a outwardly convex relative to the connector 31 of the holder 30.

The convex surface 33a is, for example, a circumferential surface with a rotation axis of the connector 31 as a central axis. That is, in a cross sectional view perpendicular to the central axis, the central axis and each point on the convex surface 33a are arranged so that a distance therebetween is substantially constant. Here, the arrangement is not limited to the one in which the distance between the central axis and each point on the convex surface 33a is constant. Specifically, the convex surface 33a may be formed so that a variation in the distance between the central axis and each point on the convex surface 33a is within the permissible range R.

Here, an example of the permissible range R may be a range in which the amount of change in angle between the long portion 12 of the body 10 and the operation part 20, based on the variation in the distance between the central axis and each point on the convex surface 33a, is less than a minimum value of the amount of change in angle detectable by the detector 10A.

The transmitting portion 35 is a flat portion to be in contact with the operator's finger, e.g. the index finger. The transmitting portion 35 is a surface opposite the contact portion 33 of the holder 30. That is, in the holder 30, the transmitting portion 35 is located opposite the contact portion 33 relative to the connector 31.

2. Action

Figure 6A:
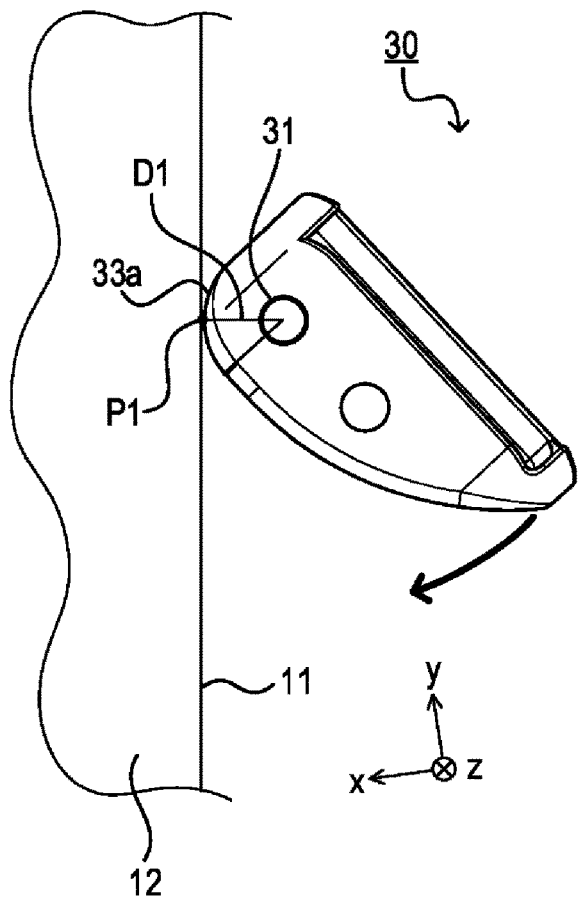
FIG. 6A and FIG. 6B show the holder before and after movement, according to some embodiments.
Figure 6B:
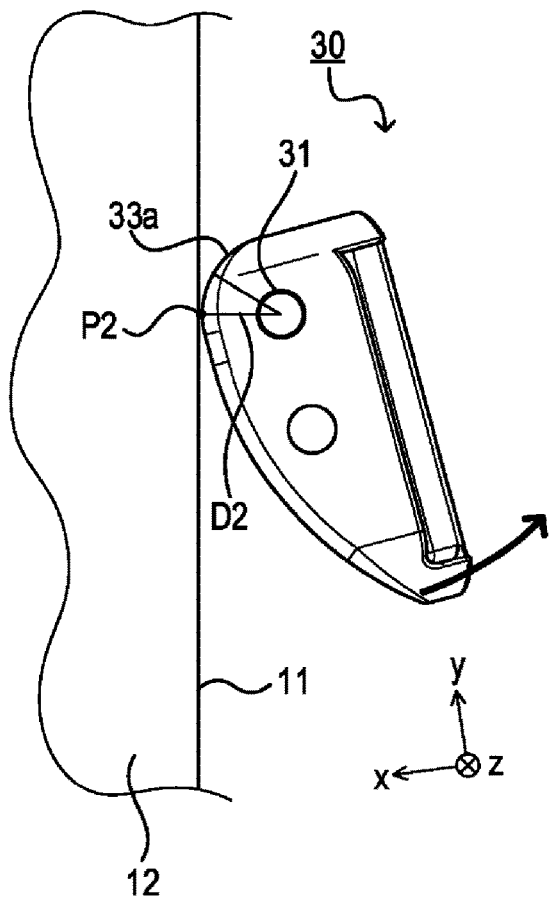

FIGS. 6A-6B show states where the holder 30 rotates around the rotation axis of the connector 31 while the contact portion 33 of the holder 30 is in contact with the body right surface 11 of the long portion 12 of the body 10. For example, when the holder 30 rotates around the rotation axis of the connector 31, the state thereof changes between a state shown in FIG. 6A and a state shown in FIG. 6B.

In the state of FIG. 6A, on a surface of the convex surface 33a, a point in contact with the body right surface 11 is assumed as a first contact point P1, and a distance from the center of the rotation axis of the connector 31 to the first contact point P1 is assumed as a first contact distance D1. When the holder 30 is rotated around the rotation axis of the connector 31, in the state of FIG. 6B and on the surface of the convex surface 33a, a point in contact with the body right surface 11 is assumed as a second contact point P2, and a distance from the center of the rotation axis of the connector 31 to the second contact point P2 is assumed as a second contact distance D2.

Here, the convex surface 33a is formed into a shape that is a circumferential surface around the rotation axis, and thus, the first contact distance D1 and the second contact distance D2 are the same. In other words, between the state shown in FIG. 6A and the state shown in FIG. 6B, a distance between the center of the rotation axis and the body 10 does not change even if the holder 30 is rotated around the rotation axis of the connector 31. Therefore, a distance between the operation part 20 connected by the connector 31 and the body 10 also does not change due to the rotation.

That is, the amount of change in the relative arrangement position of the body 10 and the operation part 20, based on the variation in the distance between the convex surface 33a and the central axis that is the center of the posture change of the holder 30 in the connector 31, is within a specified permissible range R. In the relative arrangement position of the body 10 in contact with the portion 33 and the operation part 20, when the relative posture of the holder 30 and the operation part 20 are changed, the amount of change in the relative arrangement position of the body 10 and the operation part 20 is within the specified permissible range R.

The detector 10A detects a change in the grasping operation based on the amount of change in the relative arrangement position of the body 10 and the operation part 20. Thus, the detector 10A does not detect a change in the grasping operation performed by the operator. As a result, there is no change in the control by the controller 200, which performs the control based on the change in the grasping operation detected by the detector 10A. Therefore, there is no change in the control of the slave device 300 in response to the rotation.

That is, even if the holder 30 is rotated by an unintentional operation due to a force applied to the operator's finger touching the transmitting portion 35 in a state where the contact portion 33 of the holder 30 is in contact with the body 10, it is easy to inhibit a change in the grasping by the slave device 300.

3. Effects

In the medical operation apparatus 101, the connector 31 comprises the rotation axis, and the holder 30 rotates around the rotation axis, thereby making it possible to cope with the posture change of the fingers.

This configuration allows the connector 31 to support the relative posture of the holder 30 and the operation part 20 so as to change the relative posture in accordance with the posture change of the operator's fingers.

The connector 31 is arranged so as to be movable along the longitudinal direction of the operation part 20, and thus adjustable for multiple operators with different finger sizes.

Furthermore, in a state where the contact portion 33 is in contact with the body 10, there is a possibility that the operator may perform an unintentional operation due to a force applied to the fingers, and the posture of the operator's fingers and the relative posture of the holder 30 and the operation part 20 may be changed. When the relative posture of the holder 30 and the operation part 20 is changed, the distance between the rotation axis of the connector 31 and the contact point is unchanged against the change in the position of the contact point. That is, the amount of change in the relative arrangement position of the body 10 and the operation part 20 is within the specified permissible range R.

This configuration makes it possible to inhibit the operation part 20 from moving equal to or more than the permissible range R when the unintentional operation by the operator is performed, and makes it easy to inhibit the operation part 20 from moving equal to or more than the permissible range R.

Figure 8A:
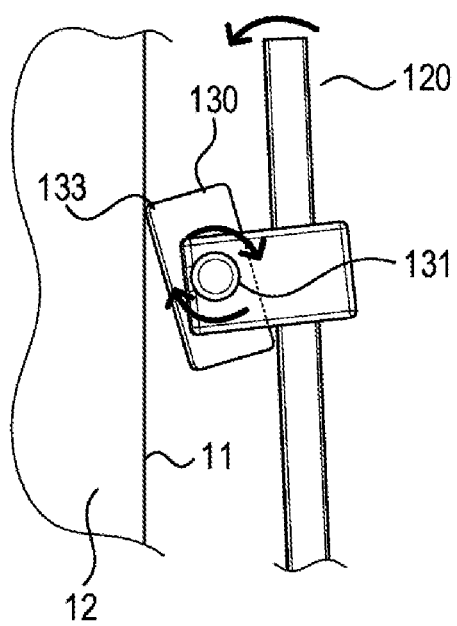
FIG. 8A and FIG. 8B show a movement of a medical operation apparatus according to the related art as a comparative example.
Figure 8B:
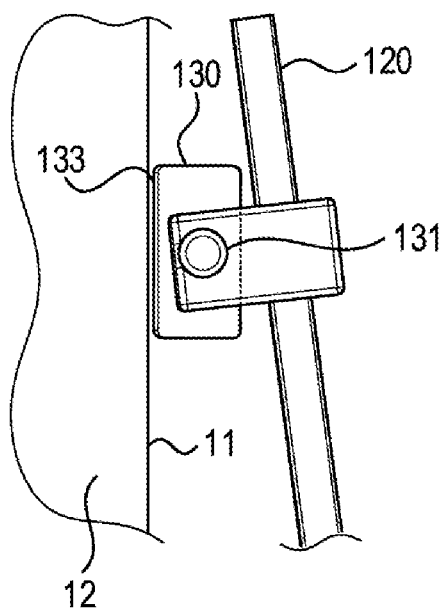

Specifically, FIG. 8 shows a comparative example, in which the holder 130 is formed into a rectangular parallelepiped shape and a body 110 comprises a flat side surface in a part to be in contact with a contact portion 133 of the holder 130. In the case shown in FIG. 8, the holder 130 rotates around the connector 131 in a contact state as shown in FIG. 8A and FIG. 8B. Then, with the rotation of the holder 130, a leading end of the operation part 120 is moved. When a sensor of a detector detects this movement, a controller controls the slave device 300 in accordance with the grasping operation detected by the detector.

Thus, in the contact state, when the holder 130 is rotated around the connector 131 by the unintentional operation by the operator, the slave device 300 is controlled based on the unintentional operation, and the slave device 300 will perform an unintentional operation.

The type of surgery for which the surgical assist robot 1 may be used is not particularly limited. However, when the surgical assist robot 1 is used for surgery requiring an operation to grasp targets that are different in hardness, such as blood vessels and organs, an unintentional operation is especially likely to occur. Therefore, the surgical assist robot 1 is suitable for use in surgery requiring an operation to grasp targets that are different in hardness.

In some embodiments, even if the unintentional operation by the operator is reflected in the state where the holder 30 is in contact with the body 10, the amount of change in the relative arrangement position of the body 10 and the operation part 20 is within the specified permissible range R.

This configuration makes it possible to inhibit an unintentional grasping operation from being reflected in the detector 10A. As a result, it is possible to easily inhibit the slave device 300 from performing an unintentional operation based on the unintentional grasping operation.

4. Modified Examples (1) In some embodiments, the convex surface 33a forms the circumferential surface around the central axis of the connector 31. However, the shape of the convex surface 33a is not limited to the circumferential surface around the central axis of the connector 31. For example, the connector 31 may be configured to have a specified center point and form a spherical shape around the center point like a sphere joint or a ball joint.

Furthermore, in some embodiments, the distance from the central axis of the connector 31 to the convex surface 33a is constant in a cross section perpendicular to the central axis of the connector 31. However, in some embodiments, the distance from the central axis of the connector 31 to the convex surface 33a is not necessarily constant, and may be varied within the permissible range R. Here, in some embodiments, the permissible range R is exemplified as a range in which the amount of change in angle between the long portion 12 of the body 10 and the operation part 20, based on the variation in the distance between the central axis and each point on the convex surface 33a, is less than the minimum value of the amount of change in angle detectable by the detector 10A. That is, the permissible range R is set to a value less than the minimum value of the amount of change detectable by the detector 10A.

Thus, it is possible to inhibit the operation part from moving equal to or more than the minimum value of the amount of change detectable by the detector 10A in response to the unintentional operation by the operator. This configuration makes it easy to inhibit the detector 10A from detecting the unintentional operation by the operator as the grasping operation.

In other words, the amount of change in the relative arrangement position of the body 10 and the operation part 20, based on the variation in the distance between the convex surface 33a of the contact portion 33 and the center of the posture change of the holder 30 in the connector 31, is within the specified permissible range R. This configuration makes it is easy to inhibit the unintentional operation by the operator from being reflected as the grasping operation.

Figure 7A:
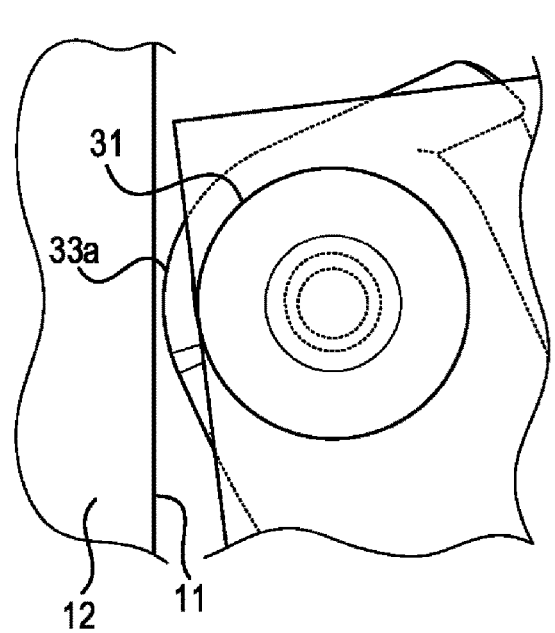
FIG. 7A and FIG. 7B show, respectively, the medical operation apparatus according to some embodiments, and a medical operation apparatus in a modified example, according to some embodiments.
Figure 7B:
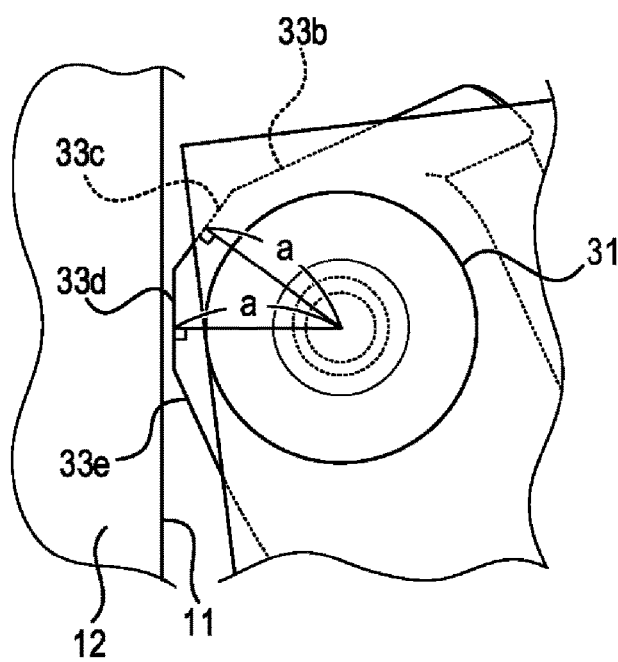

(2) In some embodiments, as shown in FIG. 7A, the contact portion 33 comprises the convex surface 33a that is a circumferential surface. However, in some embodiments, the configuration is not limited to the one comprising the circumferential surface. As shown in FIG. 7B, the contact portion 33 may comprise holder-side contact flat surfaces 33b-33e. The variation in a distance between each of the holder-side contact flat surfaces 33b-33e and the central axis of the connector 31 that is the center of the posture change of the holder 30 in the connector 31 may be within the permissible range R.

That is, based on the variation in the above distance, the variation in the distance between the central axis of the connector 31 and the body 10 may be configured to be within the permissible range R in a state where one of the holder-side contact flat surfaces 33b-33e of the contact portion 33 is in contact with the body 10 and a in state where any other surface is in contact with the body 10.

With this configuration, the amount of change in the relative arrangement position of the body 10 and the operation part 20, based on the variation in the distance between each of the holder-side contact flat surfaces 33b-33e of the contact portion 33 and the center of the posture change of the holder 30 in the connector 31, is within the specified permissible range R. This configuration makes it is easy to inhibit the unintentional operation by the operator from being reflected as the grasping operation.

Note that the number of the holder-side contact flat surfaces 33b-33e is not limited to four as shown in FIG. 7, and in some embodiments, the number may be four or more and four or less.

(3) In some embodiments, a configuration has been explained in which the operator operates the device with the right hand. However, the medical operation apparatus 101 is not limited to the configuration applied to the right-handed operation. That is, in some embodiments, the device may be applicable to a left-handed operation. In this case, for example, each component constituting the medical operation apparatus 101 may be relatively arranged so as to be operated with the left hand. Specifically, the components of the medical operation apparatus 101 may be arranged to have a positional relationship that is mirrored relative to a y-z flat surface.

(4) In some embodiments, the sensor of the detector 10A is an angle sensor. However, in some embodiments, the sensor of the detector 10A is not limited to the angle sensor. The sensor may be any sensor that can detect the arrangement position of the operation part 20 relative to the body 10. For example, various kinds of sensors including a position sensor may be used.

(5) In some embodiments, the contact portion 33 of the holder 30 comprises the convex surface 33a. This configuration makes it possible not to change the distance between the body 10 and the operation part 20 even if the holder 30 rotates around the central axis of the connector 31 in response to the posture change of the operator's fingers in a state where the convex surface 33a is in contact with the body 10. However, the configuration in which the distance between the body 10 and the operation part 20 does not change is not limited to the configuration in which the holder 30 comprises the convex surface 33a.

Figure 9:
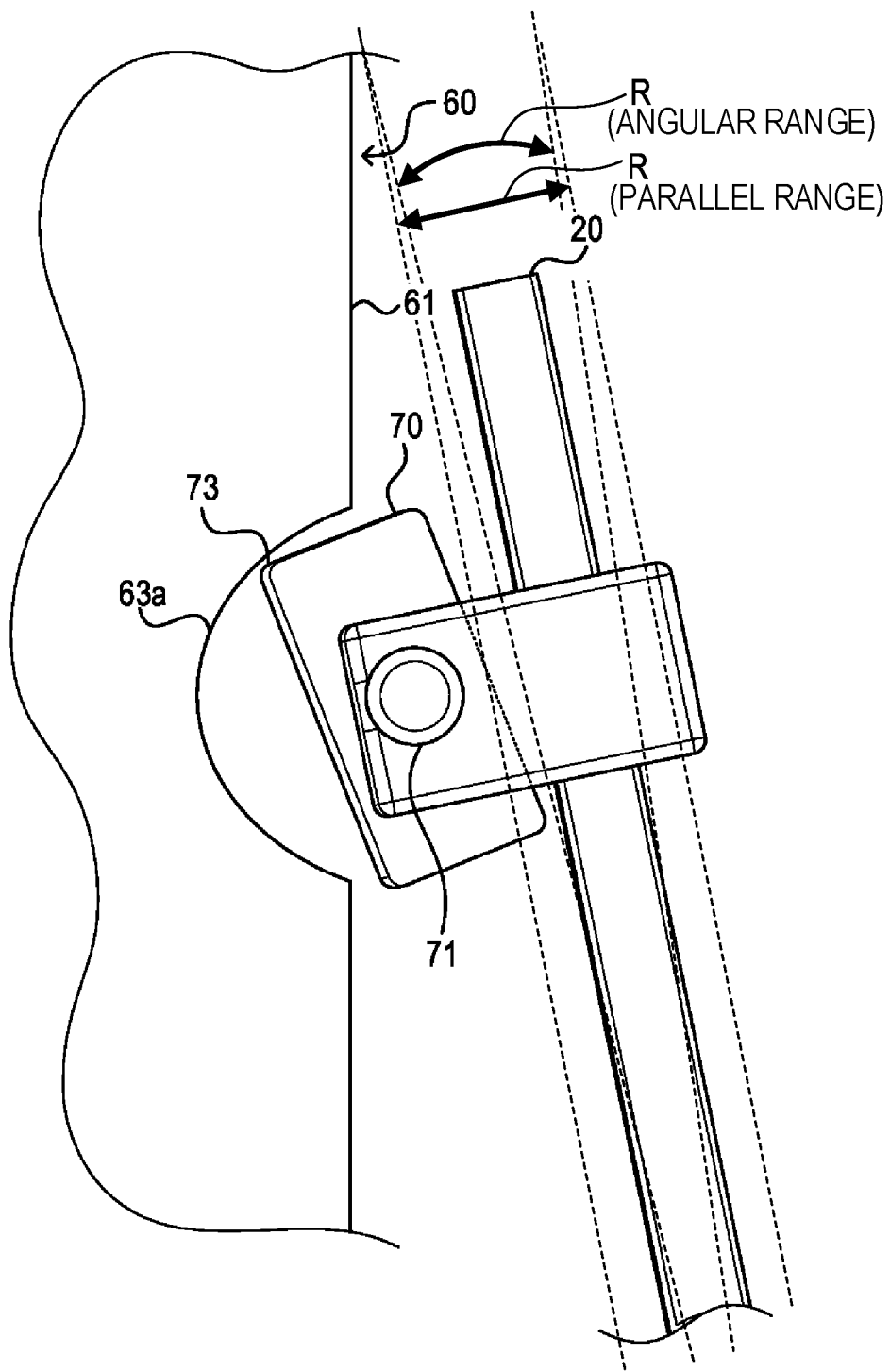
FIG. 9 shows an overview of a medical operation apparatus in a modified example, according to some embodiments.

For example, as shown in FIG. 9, in some embodiments, the body 60 may be formed to comprise, on a body right surface 61 of the body 60, a concave surface 63a concavely formed in an area to be in contact with the contact portion 33. The shape of a contact portion 73 of a holder 70 may be formed into a shape corresponding to the concave surface 63a of the body 60.

Specifically, the concave surface 63a may be formed into a shape allowing the distance between a contact point and the rotation axis of the connector 71a to be constant assuming that a point where the concave surface 63a is in contact with the contact portion 73 as the contact point when the contact portion 73 of the holder 70 is in contact with the concave surface 63a. The holder 70 may be formed into a shape, such as a rectangular parallelepiped shape, in which the contact portion 73 does not comprise the convex surface 33a, for example.

That is, the concave surface 63a may be configured such that the amount of change in the relative arrangement position of the body 10 and the operation part 20, based on the variation in the distance between the concave surface 63a and the center of the posture change of the holder 30 in the connector 31, is within the permissible range R when the contact portion 73 of the holder 70 is in contact with the concave surface 63a.

With this configuration, when the contact portion 33 is in contact with the concave surface 63a formed into a curved surface in the body 10, the amount of change in the relative arrangement position of the body 10 and the operation part 20, based on the variation in the distance between the concave surface 63a and the center of the posture change of the holder 30 in the connector 31, is within the specified permissible range R.

This configuration makes it is easy to inhibit the unintentional operation by the operator from being reflected as the grasping operation.

The concave surface 63a is not limited to a shape allowing a distance between the contact point and the rotation axis of the connector 71 to be constant assuming that the point where the concave surface 63a is in contact with the contact portion 73 as the contact point when the contact portion 73 of the holder 70 is in contact with the concave surface 63a. That is, the shape of the concave surface 63a may be any shape if the variation in the distance between the contact point and the connector 71 of the rotation axis is within the permissible range R.

Figure 10:
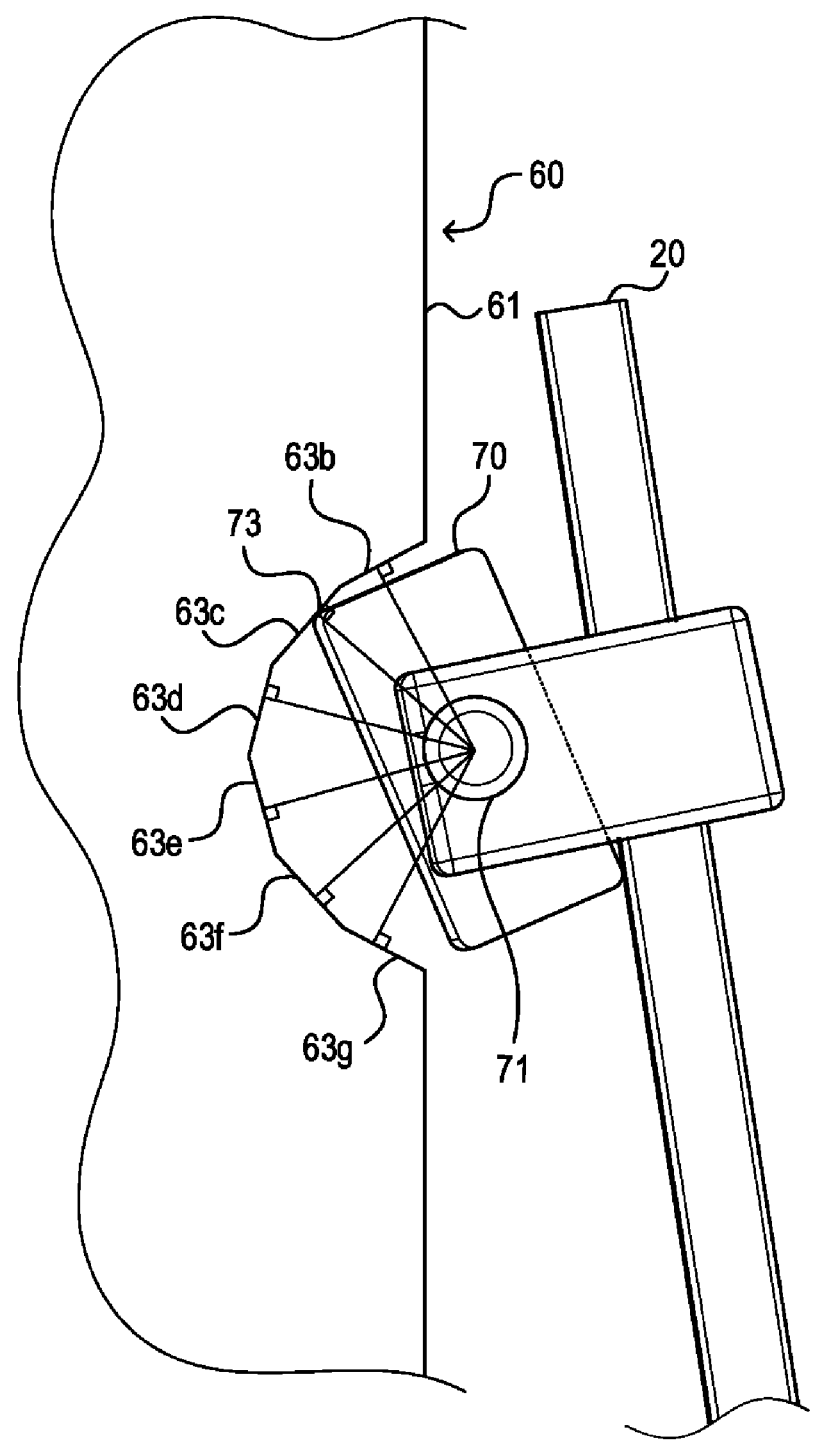
FIG. 10 shows an overview of a medical operation apparatus in a modified example, according to some embodiments.

(6) Furthermore, as shown in FIG. 10, in some embodiments, the body 10 may comprise body contact flat surfaces 63b-63g forming a concave shape in an area to be in contact with the contact portion 33. When the contact portion 33 is in contact with any of the body contact flat surfaces 63b-63g, the amount of change in the relative arrangement position of the body 10 and the operation part 20, based on the variation in the distance between each of the body contact flat surfaces 63b-63g and the center of the posture change of the holder 30 in the connector 31, may be within the specified permissible range R.

The distance between each of the body contact flat surface 63b-63g and the center of the posture change of the holder 30 in the connector 31 as used herein may mean, for example, a length of a perpendicular line drawn from each of the body contact flat surfaces 63b-63g towards the central axis of the connector 31.

In this configuration, when the contact portion 33 is in contact with the concave surface consisting of the body contact flat surfaces 63b-63g of the body 10, the amount of change in the relative arrangement position of the body 10 and the operation part 20, based on the variation in the distance between each of the body contact flat surfaces 63b-63g and the center of the posture change of the holder 30 in the connector 31, is within the specified permissible range R. This configuration makes it is easy to inhibit the unintentional operation by the operator from being reflected as the grasping operation.

(7) Note that the number of the body contact flat surfaces 63b-63g is not limited to six as shown in FIG. 10, and in some embodiments, the number may be six or more and six or less.

(8) A plurality of functions of one element of the aforementioned embodiments may be performed by a plurality of elements, and one function of one element may be performed by a plurality of elements. Furthermore, a plurality of functions of a plurality of elements may be performed by one element, and one function performed by a plurality of elements may be performed by one element. A part of the configurations of the aforementioned embodiments may be omitted. Furthermore, at least a part of the configurations of the aforementioned embodiments may be added to or replaced with the configurations of the other above-described embodiments.

(9) Other than the medical operation apparatus 101 and the surgical assist robot 1, the present disclosure may also be embodied in various forms, such as a system comprising the medical operation apparatus 101 and the surgical assist robot 1, a program to functionalize a computer as the medical operation apparatus 101 and the surgical assist robot 1, a non-transitory tangible recording medium such as a semiconductor memory storing the program, and a method for operating the medical operation apparatus 101 and the surgical assist robot 1.

It should be understood that embodiments are not limited to the various embodiments described above, but various other changes and modifications may be made therein without departing from the spirit and scope thereof as set forth in appended claims.

What is claimed is:

1. A medical operation apparatus comprising:
    a body to be grasped by an operator;
    an operation part arranged to enable at least a part of the operation part to be moved, by the operator, closer to and away from the body; and
    a holder configured to hold fingers of the operator grasping the body, the holder being configured to transmit a movement of the fingers to the operation part,
    wherein the holder comprises:
        a contact portion configured to be in contact with the body when the operation part is moved closer to the body, and
        a connector supporting a relative posture of the holder and the operation part so as to change the relative posture in accordance with a posture change of the fingers of the operator, and
    wherein, in a relative arrangement position of the operation part and the body with which the contact portion is in contact, when the relative posture of the holder and the operation part is changed, an amount of change in the relative arrangement position of the body and the operation part is within a specified permissible range.

2. The medical operation apparatus according to claim 1, further comprising a sensor configured to detect the relative arrangement position of the operation part relative to the body,
    wherein the specified permissible range is less than a minimum value of a detectable amount of change, detectable by the sensor, between the body and the operation part.

3. The medical operation apparatus according to claim 2,
    wherein the contact portion comprises a convex surface formed into a convex shape, and
    wherein the amount of change in the relative arrangement position of the body and the operation part, based on a variation in a distance between the convex surface and a center of a posture change of the holder in the connector, is within the specified permissible range.

4. The medical operation apparatus according to claim 2,
    wherein the contact portion comprises a plurality of contact flat surfaces, and
    wherein the amount of change in the relative arrangement position of the body and the operation part, based on a variation in a distance between each of the plurality of contact flat surfaces and a center of a posture change of the holder in the connector, is within the specified permissible range.

5. The medical operation apparatus according to claim 2,
    wherein the body comprises a concave surface formed into a concave shape in an area to be in contact with the contact portion, and
    wherein, when the contact portion is in contact with the concave surface, the amount of change in the relative arrangement position of the body and the operation part, based on a variation in a distance between the concave surface and a center of a posture change of the holder in the connector, is within the specified permissible range.

6. The medical operation apparatus according to claim 2,
    wherein the body comprises a plurality of body flat surfaces forming a concave shape in an area to be in contact with the contact portion,
    when the contact portion is in contact with any of the plurality of body flat surfaces, the amount of change in the relative arrangement position of the body and the operation part, based on a variation in a distance between each of the plurality of body flat surfaces and a center of a posture change of the holder in the connector, is within the specified permissible range.

7. The medical operation apparatus according to claim 1,
    wherein the contact portion comprises a convex surface formed into a convex shape, and
    wherein the amount of change in the relative arrangement position of the body and the operation part, based on a variation in a distance between the convex surface and a center of a posture change of the holder in the connector, is within the specified permissible range.

8. The medical operation apparatus according to claim 1,
    wherein the contact portion comprises a plurality of contact flat surfaces, and
    wherein the amount of change in the relative arrangement position of the body and the operation part, based on a variation in a distance between each of the plurality of contact flat surfaces and a center of a posture change of the holder in the connector, is within the specified permissible range.

9. The medical operation apparatus according to claim 1,
    wherein the body comprises a concave surface formed into a concave shape in an area to be in contact with the contact portion, and
    wherein, when the contact portion is in contact with the concave surface, the amount of change in the relative arrangement position of the body and the operation part, based on a variation in a distance between the concave surface and a center of a posture change of the holder in the connector, is within the specified permissible range.

10. The medical operation apparatus according to claim 1,
    wherein the body comprises a plurality of body flat surfaces forming a concave shape in an area to be in contact with the contact portion,
    when the contact portion is in contact with any of the plurality of body flat surfaces, the amount of change in the relative arrangement position of the body and the operation part, based on a variation in a distance between each of the plurality of body flat surfaces and a center of a posture change of the holder in the connector, is within the specified permissible range.

11. The medical operation apparatus according to claim 1,
    wherein the operation part is formed into a long shape, and
    wherein the connector connects the holder and the operation part so that an arrangement position of the holder along a longitudinal direction of the operation part having a long shape is changeable.

12. A medical operation apparatus comprising:
a body;
an operation part connected to the body such that at least a portion of the operation part is movable with respect to the body; and
a finger holder configured to receive fingers of an operator who grasps the body, the finger holder configured to transmit a movement of the fingers to the operation part and comprising:
a contact portion configured to contact with the body when the operation part is moved toward the body, and
a connector rotatably supporting the contact portion,
wherein, when the operation part contacts the body and a relative posture of the finger holder and the operation part is changed, an amount of change in a relative position of the body relative to the operation part is within a threshold range.

13. The medical operation apparatus according to claim 12, further comprising a sensor configured to detect the relative position,
wherein the threshold range is less than a minimum value of a detectable amount of change between the body and the operation part that is detectable by the sensor.

14. The medical operation apparatus according to claim 12,
wherein the contact portion comprises a convex surface, and
the amount of change is based on a variation in a distance between the convex surface and a central axis of the connector.

15. The medical operation apparatus according to claim 12,
wherein the contact portion comprises a plurality of contact flat surfaces, and
the amount of change is based on a variation in a distance between each of the plurality of contact flat surfaces and a central axis of the connector.

16. The medical operation apparatus according to claim 12,
wherein the body comprises a concave surface in an area to be in contact with the contact portion, and
wherein the amount of change is on a variation in a distance between the concave surface and a central axis of the connector.

17. The medical operation apparatus according to claim 12,
wherein the body comprises a plurality of body flat surfaces forming a contiguous concave surface in an area to be in contact with the contact portion, and
the amount of change is based on a variation in a distance between each of the plurality of body flat surfaces and a central axis of the connector.

18. The medical operation apparatus according to claim 12,
wherein the operation part comprises a shaft, and
the connector connects the finger holder and the operation part so that an arrangement position of the finger holder along a longitudinal direction of the shaft is changeable.

19. A medical operation apparatus comprising:
a body including a shaft and a cylindrical grip attached to one end of the shaft;
an operating part movable relative to the body;
a finger holder that is slidable along the operating part, the finger holder comprising a connector, and a contact portion that is rotatably connected to the connector and that contacts the shaft of the body when the operating part is moved relative to the body,
wherein, when the contact portion contacts the shaft, the contact portion is rotatable such that a distance between a central axis of the connector and a contact point between the contact portion and the shaft remains constant.

20. The medical operation apparatus according to claim 19, wherein the contact portion has a convex surface that faces the shaft of the body.

* * * * *